(12) United States Patent
Greenbaum et al.

(10) Patent No.: US 6,649,417 B2
(45) Date of Patent: Nov. 18, 2003

(54) TISSUE-BASED STANDOFF BIOSENSORS FOR DETECTING CHEMICAL WARFARE AGENTS

(75) Inventors: Elias Greenbaum, Oak Ridge, TN (US); Charlene A. Sanders, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 358 days.

(21) Appl. No.: 09/819,511

(22) Filed: Mar. 28, 2001

(65) Prior Publication Data

US 2002/0142472 A1 Oct. 3, 2002

Related U.S. Application Data

(60) Provisional application No. 60/226,646, filed on Aug. 21, 2000.

(51) Int. Cl.$^7$ .............................. G01N 21/76; G01N 1/22
(52) U.S. Cl. .................... 436/172; 436/164; 436/167; 436/181; 422/82.05; 422/82.08; 422/83; 422/88; 435/287.1; 435/288.7; 435/808
(58) Field of Search ..................... 436/63, 164, 167, 436/169, 172, 181; 422/55, 56, 58, 82.05, 82.08, 83, 88, 98; 435/287.1, 288.7, 808, 34

(56) References Cited

U.S. PATENT DOCUMENTS

| | | | |
|---|---|---|---|
| 4,500,641 A | 2/1985 | van den Engh | |
| 4,549,427 A | * 10/1985 | Kolesar, Jr. | 73/24.01 |
| H454 H | 4/1988 | Sickenberger et al. | 73/27 |
| 4,752,226 A | 6/1988 | Akers et al. | 434/11 |
| 4,768,390 A | * 9/1988 | Baker et al. | 73/865.6 |
| 4,906,440 A | 3/1990 | Kolesar | 422/98 |
| 4,942,303 A | 7/1990 | Kolber | |
| 5,014,225 A | * 5/1991 | Vidaver et al. | 702/19 |
| H1344 H | 8/1994 | Baldauf | 435/20 |
| 5,866,430 A | 2/1999 | Grow | 436/172 |
| 5,874,046 A | 2/1999 | Megerle | |
| 5,922,183 A | 7/1999 | Rauh | 204/403 |
| 5,965,882 A | 10/1999 | Megerle et al. | 250/287 |
| 6,083,740 A | * 7/2000 | Kodo et al. | 435/266 |
| 6,119,976 A | * 9/2000 | Rogers | 244/13 |
| 6,121,053 A | 9/2000 | Kolber | |
| 6,187,530 B1 | 2/2001 | Scholin et al. | |
| 6,316,268 B1 | * 11/2001 | Yang et al. | 436/106 |
| 6,402,031 B1 | * 6/2002 | Hall | 235/400 |

FOREIGN PATENT DOCUMENTS

| | | | |
|---|---|---|---|
| CA | 2265304 | * | 3/1999 |
| DE | 248433 A1 | | 8/1987 |
| DE | 19857792 A1 | | 7/2000 |
| EP | 0811842 A1 | | 12/1997 |
| WO | WO 99/32876 | | 7/1999 |

OTHER PUBLICATIONS

Krause, G. H. and Weis, E., (1991) Chlorophyll fluorescence and photosynthesis: the basics, *Annu. Rev. Plant Physiol. Plant Mol. Biol.* 42: 313–349.

(List continued on next page.)

*Primary Examiner*—Maureen M. Wallenhorst
(74) *Attorney, Agent, or Firm*—Joseph A. Marasco

(57) ABSTRACT

A tissue-based, deployable, standoff air quality sensor for detecting the presence of at least one chemical or biological warfare agent, includes: a cell containing entrapped photosynthetic tissue, the cell adapted for analyzing photosynthetic activity of the entrapped photosynthetic tissue; means for introducing an air sample into the cell and contacting the air sample with the entrapped photosynthetic tissue; a fluorometer in operable relationship with the cell for measuring photosynthetic activity of the entrapped photosynthetic tissue; and transmitting means for transmitting analytical data generated by the fluorometer relating to the presence of at least one chemical or biological warfare agent in the air sample, the sensor adapted for deployment into a selected area.

8 Claims, 5 Drawing Sheets

OTHER PUBLICATIONS

Krause, G. H., Vernotte, C., and Briantais, J.–M., (1982) Photoinduced quenching of cholorophyll fluorescence in intact chloroplasts and algae. *Biochimica et Biophysica Acta.* 679: 116–124.

Schreiber, U., Bilger, W., and Neubauer, C., (1994) Chlorophyll fluorescence as a nonintrusive indicator for rapid assessment of in vivo photosynthesis. *Ecological Studies* 100: 49–70.

Genty, B., Briantais, J.–M., and Baker, N. R., (1989) The relationship between the quantum yield of photosynthetic electron transport and quenching of chlorophyll fluorescence. *Biochimica et Biophysica Acta.* 990:87–92.

Van Kooten and Snel (1990) tabulated the use of chlorophyll fluorescence nomenclature in plant stress physiology. ??.

Edwards, G. E. and Baker, N. R., (1993) Can $CO_2$ assimilation in maize leaves by predicted accurately from chlorophyll fluorescence analysis? *Photo. Res.* 37:89–102.

Seaton, G. G. R. and Walker, D. A., (1995) Chlorophyll fluorescence as a measure of photosynthetic carbon assimilation. *Proc. R. Soc. London Ser. B.* 242: 99–108.

Naessens, M., Leclerc J.C., Tran–Minh, C. (2000) Fiber optic biosensor using *Chlorella vulgaris* for determination of toxic compounds. Ecotoxicol. Environ. Saf., 46, 181–185.

Internet Web Site http://www.walz.com e.g., http://www.walz.com/xepam.htm and http://www.walz.com/pamzta.htm.

* cited by examiner-

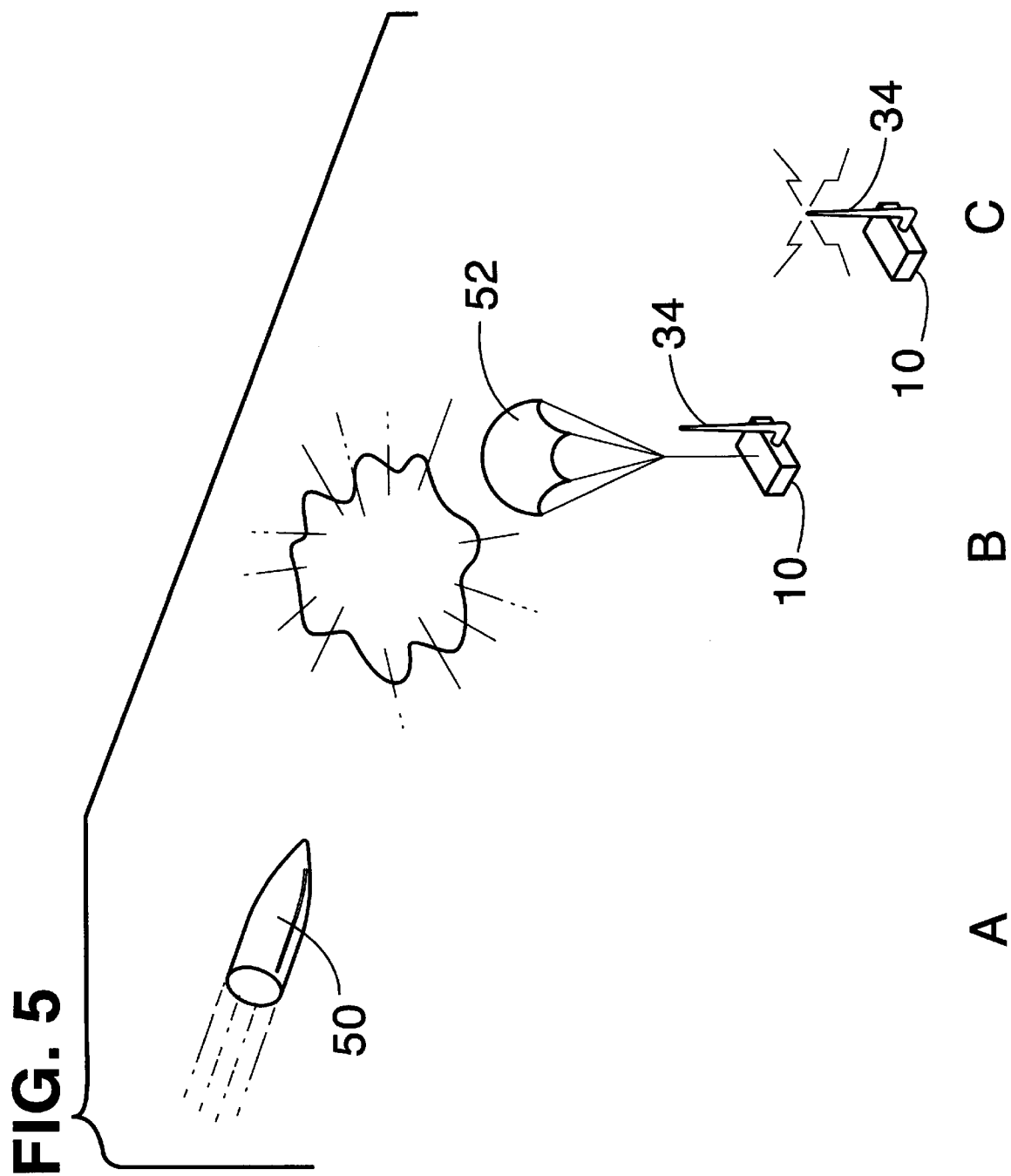

TISSUE-BASED STANDOFF BIOSENSORS FOR DETECTING CHEMICAL WARFARE AGENTS

CROSS-REFERENCE TO RELATED APPLICATION

This application claims the benefit of U.S. Provisional Application No. 60/226,646, filed on Aug. 21, 2000, the entire disclosure of which is incorporated herein by reference.

The United States Government has rights in this invention pursuant to contract no. DE-AC05-00OR22725 between the United States Department of Energy and UT-Battelle, LLC.

FIELD OF THE INVENTION

The present invention relates to standoff sensors for detecting chemical and/or biological warfare agents, and more particularly to deployable standoff sensors based on changes of quantum yield of fluorescence in which photosynthetic tissue is used as a sensor material for detecting chemical and/or biological warfare agents in air.

BACKGROUND OF THE INVENTION

Standoff sensors have been used as chemical warfare sensors and detectors. Currently available standoff sensor technology is based generally on adaptations, modifications, and extensions of conventional analytical chemistry equipment and techniques. Some examples follow.

U.S. Pat. No, 5,965,882 issued on Oct. 12, 1999 to Megerle et al. describes a miniaturized ion mobility spectrometer sensor cell that comprised an improved spectrometer for detecting chemical warfare agents and hazardous vapors.

U.S. Pat. No. 5,922,183 issued on Jul. 13, 1999 to Rauh describes a metal oxide matrix. Thin film composites of the oxides and biological molecules such as enzymes, antibodies, antigens and DNA strands can be used for both amperometric and potentiometric sensing.

U.S. Pat. No. 5,866,430 issued on Feb. 2, 1999 to Grow describes a methodology and devices for detecting or monitoring or identifying chemical or microbial analytes. The described methodology comprises four basic steps: (1) The gas or liquid medium to be monitored or analyzed is brought into contact with a bioconcentrator which is used to bind with or collect and concentrate one or more analytes. (2) The bioconcentrator-analyte complex is then exposed to radiation of one or more predetermined wavelengths to produce Raman scattering spectral bands. (3) At least a portion of the Raman spectral bands are collected and processed by a Raman spectrometer to convert the same into an electrical signal. And (4) the electrical signal is processed to detect and identify, qualitatively and/or quantitatively, the analyte(s).

U.S. SIR No. H1344 issued on Aug. 2, 1994 Baldauf et al describes a portable automatic sensor for toxic gases. Their method provided for the integration of a low-volume liquid flow and sampling system and a portable optical waveguide-based fluorescence detector for the chemical analysis of reagents in fluorescence-based reactions. In a preferred embodiment, the presence and concentration of acetylcholinesterase inhibitors, such as chemical warfare nerve agents or certain insecticides, is determined by mixing aqueous samples with a dilute solution of n-methyl indoxyl acetate, and monitoring the formation of a fluorescent product (n-methyl indoxyl).

U.S. Pat. No. 4,906,440 issued on Mar. 6, 1990 to Kolesar describes a sensor for detecting chemicals. In this sensor a gas detector is described that detects the presences of the gas when the gas reacts with a distributed RC notch network to cause a shift in operating frequency and notch depth. A metallic/metallic oxide gas sensitive discontinuous film acts as the distributive resistive element in the RC notch network. The gas changes the conductivity of the film and this causes the network to react. In the preferred embodiment, a copper/cuprous oxide film detects organophosphorus compounds, which can be chemical warfare agents.

U.S. Pat. No. 4,752,226 issued on Jun. 21, 1988 to Akers et al. describes a method for simulating chemical warfare attack that includes the use of a radiant energy transmitting device for radiating energy in a pattern which simulates different types and forms of chemical agents. Protective devices, such as gas masks, protective clothing, or structures, are provided with sensors for determining whether the protective device is properly employed.

U.S. SIR No. H454 issued on Apr. 5, 1988 Sickenberger, et al. describes a method of detecting leaks within artillery shells, bombs and other munitions which involves the permanent in situ insertion within the munitions cavity of an electrically resistive surface which varies in resistance with the adsorption of leaking chemical vapors. In a typical embodiment of the invention, the electrically resistive surface is serially connected with an identical surface with an inert coating and the voltage drops across both the coated and uncoated surfaces are measured.

It is well-known that there is a close correlation between photosynthetic activity and fluorescence from plants. The following scientific and technical publications are recommended for a basic understanding of the technology:

1. Krause, G. H. and Weis, E., (1991) Chlorophyll fluorescence and photosynthesis: the basics, *Annu. Rev. Plant Physiol. Plant Mol. Biol.* 42: 313–349.
2. Krause, G. H., Vernotte, C., and Briantais, J.-M., (1982) Photoinduced quenching of chlorophyll fluorescence in intact chloroplasts and algae. *Biochimica et Biophysica Acta.* 679: 116–124.
3. Schreiber, U., Bilger, W., and Neubauer, C., (1994) Chlorophyll fluorescence as a nonintrusive indicator for rapid assessment of in vivo photosynthesis. *Ecological Studies* 100: 49–70.
4. Genty, B., Briantais, J.-M., and Baker, N. R., (1989) The relationship between the quantum yield of photosynthetic electron transport and quenching of chlorophyll fluorescence. *Biochimica et Biophysica Acta.* 990:87–92.
5. Van Kooten and Snel (1990) tabulated the use of chlorophyll fluorescence nomenclature in plant stress physiology. *Photo. Res.* 25: 147–150.
6. Edwards, G. E. and Baker, N. R., (1993) Can $CO_2$ assimilation in maize leaves by predicted accurately from chlorophyll fluorescence analysis? *Photo. Res.* 37: 89–102.
7. Seaton, G. G. R. and Walker, D. A., (1995) Chlorophyll fluorescence as a measure of photosynthetic carbon assimilation. *Proc. R. Soc. London Ser. B.* 242: 99–108.
8. Naessens, M., Leclerc J. C., Tran-Minh, C. 2000. Fiber optic biosensor using *Chlorella vulgaris* for determination of toxic compounds. Ecotoxicol. *Environ. Saf,* 46, 181–185.

Naessens et al. have reported a fiber optic biosensor using entrapped *Chlorella vulgaris* for determination of toxic compounds in water. Naessens et al. uses filter paper-entrapped Chlorella and flows a water sample through the filter paper.

A treatise on chemical warfare agents may also be helpful. See, for example, Satu M. Sonami, *Chemical Warfare Agents* Academic Press, 1992.

OBJECTS OF THE INVENTION

Accordingly, objects of the present invention include: provision of a tissue-based standoff biosensor whose sensing principle is based on changes in the fluorescence induction curve and the overall quantum yield of fluorescence; a method of testing air quality in forward areas of a war zone without endangering personnel; and a method if identifying areas in a war zone that are contaminated with chemical and/or biological warfare agents. Further and other objects of the present invention will become apparent from the description contained herein.

SUMMARY OF THE INVENTION

In accordance with one aspect of the present invention, the foregoing and other objects are achieved by a tissue-based, deployable, standoff air quality sensor for detecting the presence of at least one chemical or biological warfare agent, which includes: a cell containing entrapped photosynthetic tissue, the cell adapted for analyzing photosynthetic activity of the entrapped photosynthetic tissue; means for introducing an air sample into the cell and contacting the air sample with the entrapped photosynthetic tissue; a fluorometer in operable relationship with the cell for measuring photosynthetic activity of the entrapped photosynthetic tissue; and transmitting means for transmitting analytical data generated by the fluorometer relating to the presence of at least one chemical or biological warfare agent in the air sample, the sensor adapted for deployment into a selected area.

In accordance with another aspect of the present invention, a method of testing air to detect the presence of at least one chemical or biological warfare agent includes the steps of:

a. deploying a tissue-based, deployable, standoff air quality sensor into an area of suspected presence of at least one chemical or biological warfare agent, so that the sensor, upon deployment tests the air for the presence of at least one chemical or biological warfare agent by:
  (1) contacting an air sample with photosynthetic organisms entrapped in the sensor;
  (2) analyzing photosynthetic activity of the entrapped photosynthetic organisms; and
  (3) transmitting analytical data relating to the presence of at least one chemical or biological warfare agent in the air sample; and b. receiving the data.

BRIEF DESCRIPTION OF THE DRAWINGS

FIG. 5 is an illustration of an artillery or rocket deployment of a standoff biosensor in accordance with an embodiment of the present invention. Steps A, B, and C are shown in sequence.

Figure 1:
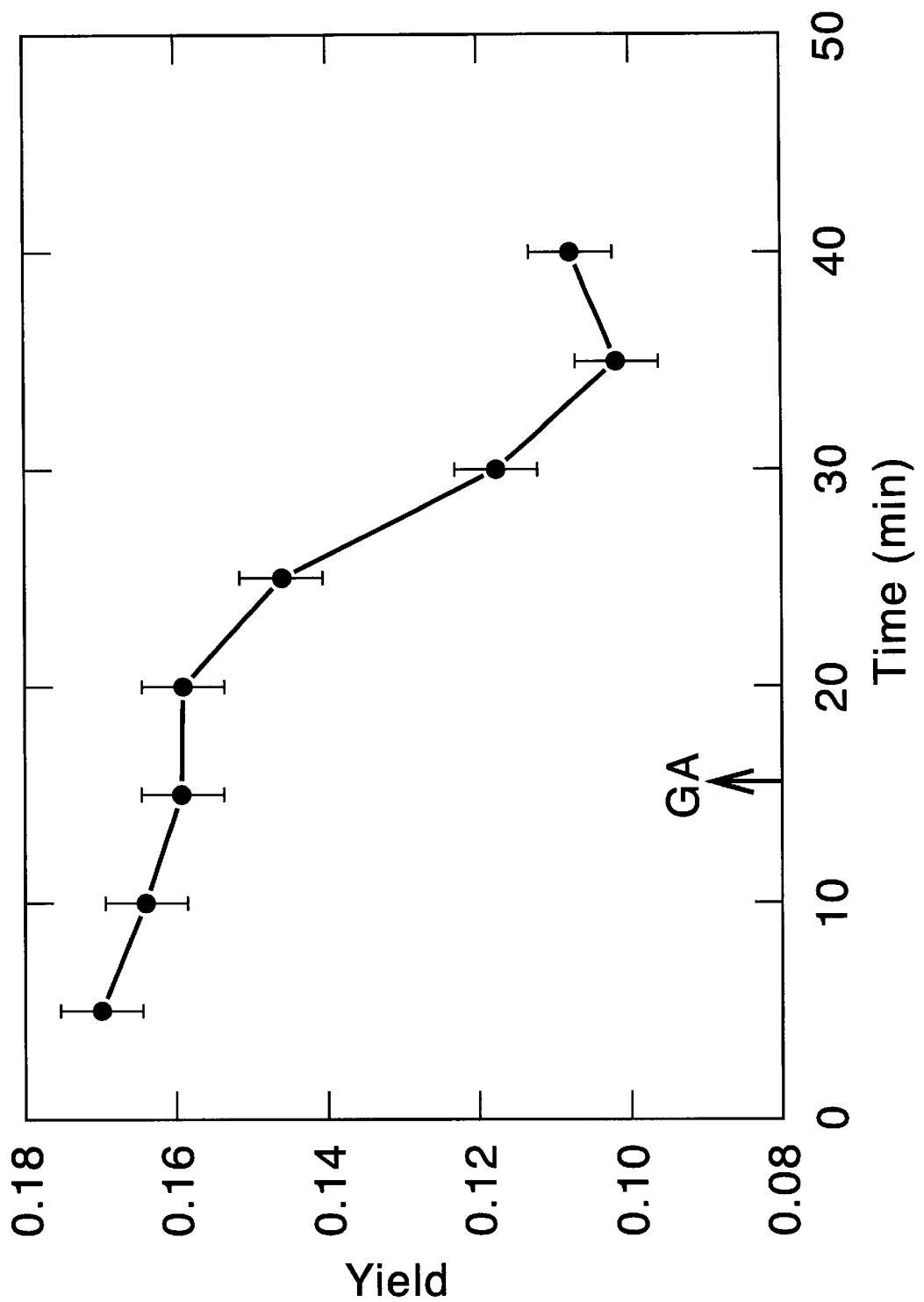
FIG. 1. is a graph illustrating the airborne detection of tabun (GA) in accordance with the present invention.

For a better understanding of the present invention, together with other and further objects, advantages and capabilities thereof, reference is prepared to the following disclosure and appended claims in connection with the above-described drawings.

DETAILED DESCRIPTION OF THE INVENTION

This invention is in the field of tissue-based biosensors. More particularly it utilizes photosynthetic microorganisms such as green algae and cyanobacteria for the detection of chemical warfare agents, particularly in forward areas where unmanned deployment is necessary to avoid possible exposure of personnel to chemical warfare agents. The principle of operation of the detector is based on the well-known scientific fact that the quantum yield of fluorescence is dependent on the ability of photosynthetic organisms to perform photosynthesis. This phenomenon is used in the present invention to construct biosensors that can be used for the rapid detection of, for example, chemical warfare agents in a battlefield. The algae are entrapped on filters and the fluorescence monitored with a compact optoelectronic recording system. This combination of entrapped algae/bacteria and detection and recording can be made so that it withstands inertial forces. The sensors can then be deployed (launched, dropped, or otherwise introduced in unmanned fashion) into suspected danger zones without endangering personnel. Combined with a conventional cell modem and conventional encrypted communications, it is possible to send coded messages to field commanders informing them of the safety of forward positions prior to movement of personnel in a war zone.

Unicellular green algae or cyanobacteria are entrapped on a bio-trap, usually a disc of filter paper. Air samples are then passed through both microorganism and filter. Any component of the air that negatively impacts photosynthetic capability will cause a change in the fluorescence induction curve, with resultant changes in the quantum yield of fluorescence. As described in further detail below, the change in fluorescence represents a decrease in photosynthetic capability. Different chemical warfare agents will have different influences on the photosynthetic apparatus of a particular alga or cyanobacterium. And the same chemical agent will affect the fluorescence of different organisms in different ways. Some will cause an increase, while others will cause a decrease in fluorescence (non-photochemical quenching of fluorescence). Specific antagonists combined with specific algae or cyanobacteria will cause characteristic changes that can be used to construct a look-up library or database of cause and effect combinations.

The entrapped algae and optoelectronic detection system can easily be constructed using conventional means to form a compact, robust, inertially hardened detection system that can be deployed by launching or dropping into suspected danger zones. The rapid response of the fluorescence emission signal, combined with a pre-deployment control fluorescence measurement followed by a second fluorescence measurement in the test zone provides a reliable assay on air quality. In a standoff embodiment, the sensor can be fitted with a cell modem and encrypted telecommunications so that all data acquisition and analysis can be performed remotely. In order to provide stability and ease of use, microorganisms that are known to be rugged and capable of extended storage are preferable. One such microorganism is the cyanobacterium, *Nostoc commune*.

Unicellular microalgae can be entrapped on filter pads without a loss of photosynthetic activity. Likewise cyanobacteria, which are well known for their tolerance to anhydrous stress, are well suited for immobilization on filter pads. Any photosynthetic organism chosen to comprise the biosensor must be robust and capable of withstanding limited periods of stress while in transit to a remote location or in storage in preparation for field deployment. Air-dried cells of *Nostoc commune*, a cyanobacterium, are known to resume lipid biosynthesis after rehydration and to recover nitrogenase activity and ATP pools after two weeks of desiccation. Rehydrated dried colonies of *N. commune* can rapidly recover respiration and photosynthesis.

The following examples illustrate the principle of for detection of chemical warfare agents.

EXAMPLE I

The invention was tested for the airborne detection of tabun (GA), a well-known nerve agent that has been used as chemical warfare agent. A "wind" of tabun was used with the help of a specially designed cell chamber. The cell chamber is a closed system aeration apparatus designed to infuse bench air through the fiberglass-entrapped biosensor at a constant rate of 200 ml/min. The sensor is housed in the top of the cell chamber on a glass frit. The humidifiers contain water for regulation of the relative humidity in the gas stream. Flow rates were adjusted with needle valves allowing alterations in the flow of air through the toxic agent while maintaining a total flow rate of 200 ml/min and relative humidity of 85%. The absolute flow rate was measured with a soap film flow meter connected to the cell chamber vent. The toxic agent in the U tube was isolated from the clean air flow path by a three-way valve while control fluorescence measurements were made. When the valve was switched, air flowed through the toxic agent tube carrying vapors directly to the sensor. Fluorescence induction curves were measured before and during exposure to toxic agents using Opti-Sciences OS1-FL and OS5-FL modulated fluorometers (Tyngsboro, Mass.). The OS1-FL is a hand-held fluorometer with a pulse modulated detection system. The modulation was adjusted so that the minimal fluorescence signal in low background laboratory light (Fs) was in the range of 90–150 relative fluorescence units. A halogen lamp from the actinic light source of a Walz XE-PAM fluorometer illuminated the sensor at an intensity of 1500 mE/m2/sec via the OS1FL fiber optic cable through a window over the sensor in the top of the cell apparatus. Fluorescence induction curves were recorded every 5 minutes and data collection for each curve were completed within 10 seconds. The OS5-FL fluorometer was fitted with an avalanche photodiode to improve signal to noise ratio. The minimal fluorescence signal was set to 130–150 relative fluorescence units in low laboratory light. Fluorescence induction curves were recorded when the sensors were illuminated from the OS5-FL fiber optic cable at 5 min. intervals (3 sec. duration) at an intensity of 1570 mE/m2/sec. Data extracted from the fluorescence induction curves were used to calculate Fs, Fmax (maximum fluorescence), Fv (variable fluorescence,=Fmax−Fs) and the efficiency of Photosystem II photochemistry (Fv/Fmax). Results of the test are shown in FIG. 1.

EXAMPLE II

Figure 2:
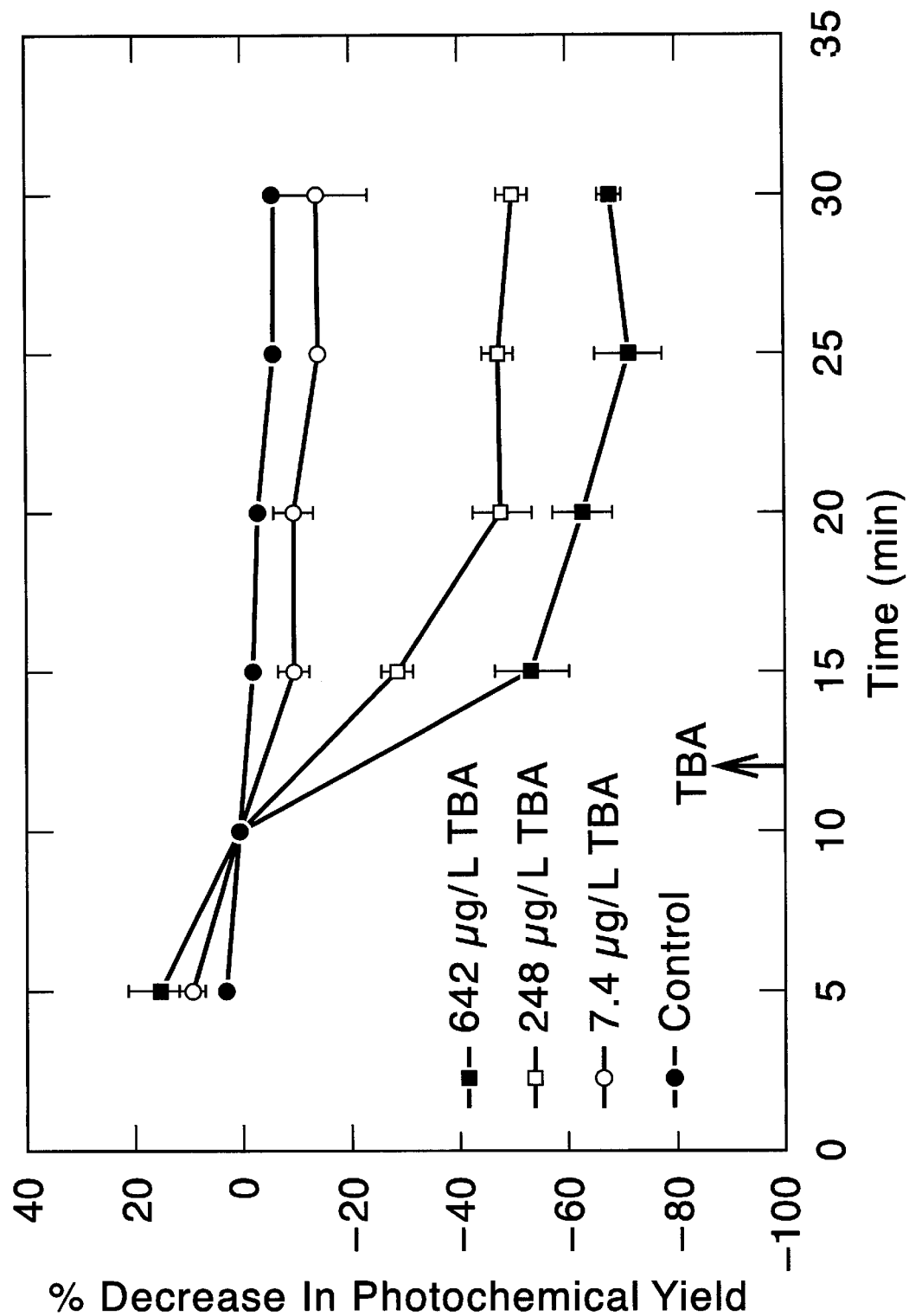
FIG. 2. is a graph illustrating the airborne detection of tributylamine (TBA), a stabilizer that is used in conjunction with the nerve agent sarin, in accordance with the present invention.

The invention was tested as in Example I for the detection of tributylamine (TBA), a stabilizer that is used in conjunction with the nerve agent sarin. The response of the Nostoc sensor to TBA was tested in the cell chamber by recording fluorescence induction curves every 5 min. during contact of the sensor with TBA. Twelve minutes into the run, TBA was introduced into the air stream. Fmax decreased and Fs increased. Dose-response curves (FIG. 2) for 7.4, 248, and 642 mg/L TBA showed a good correlation between TBA concentration and change in yield. Results of the test are shown in FIG. 2.

EXAMPLE III

Figure 3:
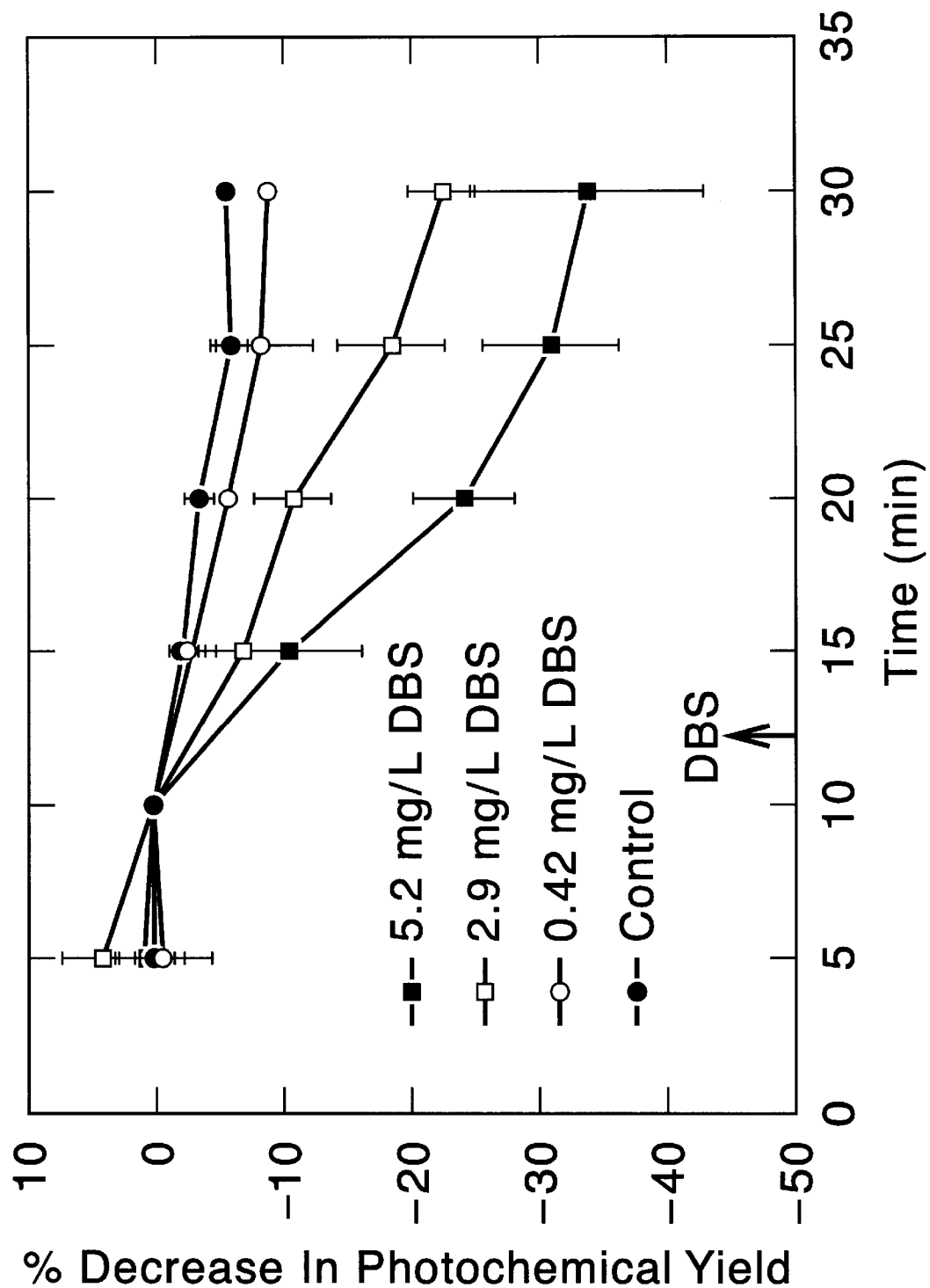
FIG. 3. is a graph illustrating the airborne detection of dibutylsulfide, a simulant of mustard gas (HD), in accordance with the present invention.

The invention was tested as in Example I for the detection of dibutylsulfide a simulant of mustard gas (HD). Fmax decreased markedly; the fluorescence yield decreased 27% from initial control values during an 18 min exposure to DBS vapor. Results of the test are shown in FIG. 3.

Figure 4:
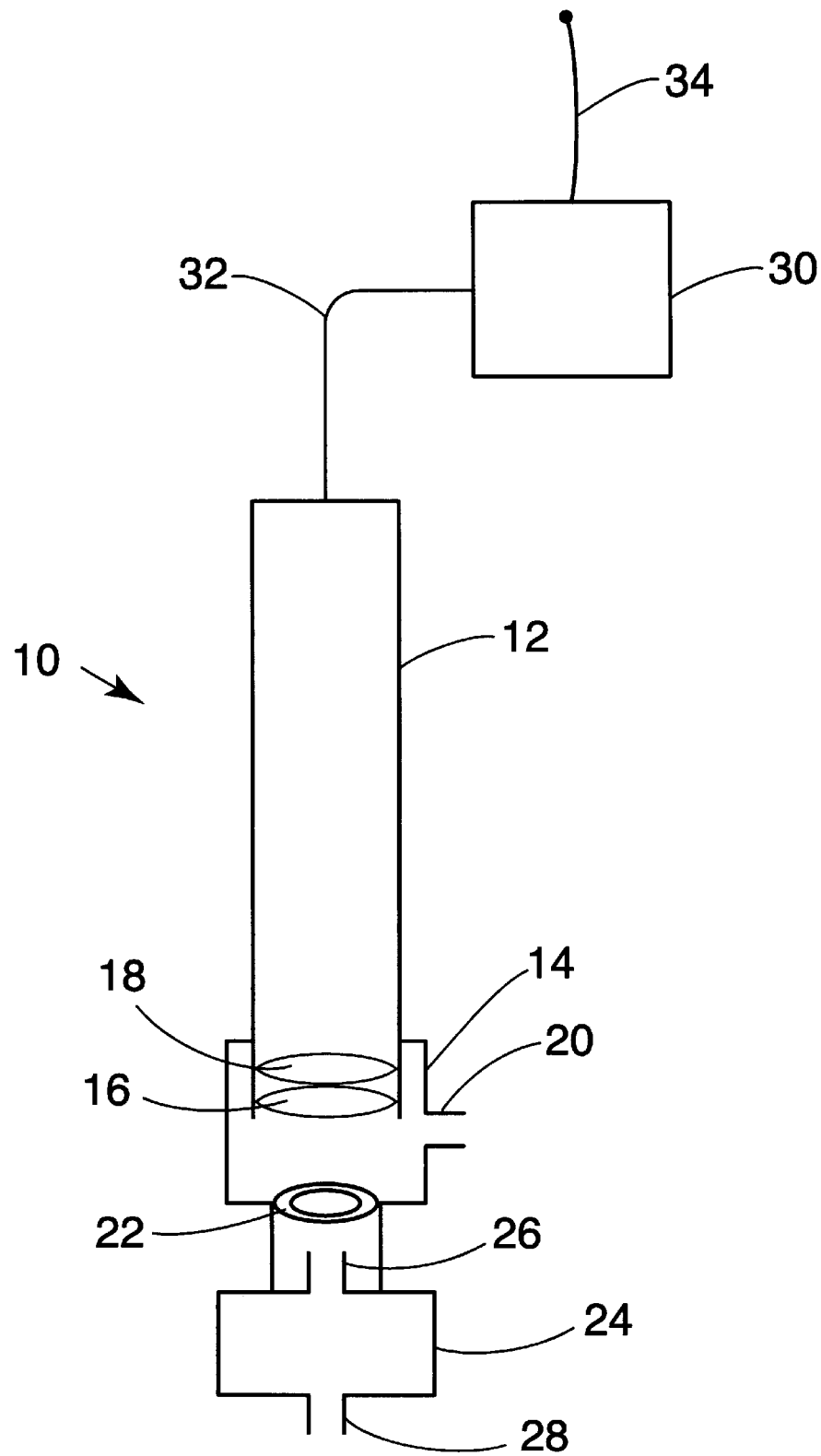
FIG. 4 is an illustration of a basic photosynthetic-tissue-based biosensor in accordance with an embodiment of the present invention.

A simple biosensor 10 for carrying out the method of present invention is shown schematically in FIG. 4. A fluorometer 12 is attached to a cell 14 so that a cell window 16 faces the fluorometer input 18. The cell has an inlet 20 for introducing an air sample into the cell 14, a bio-trap 22 containing entrapped photosynthetic tissue, and an outlet 26 for air to exit the cell 14. A pump 24 draws air from the outlet 26 and expels same through an exit 28.

The cell 14 could have a displacement pump which draws air into the cell and expels same through a common inlet/outlet opening (analogous to 20), obviating outlet 26 and exit 28. Any means for introducing air into the cell and/or discharging air from the cell is suitable for carrying out the present invention. The bio-trap 22 should face the cell window 16, and can be comprised of filter paper, glass frit, or any other porous material suitable for entrapping photosynthetic tissue while allowing air to pass therethrough.

The air sample is preferably passed through the bio-trap 22 to ensure optimum contact with the entrapped photosynthetic tissue. Passing the air sample over the surface of the bio-trap 22 would be operable, but may result in a loss of sensitivity.

The fluorometer 12 must be of sufficient sensitivity for measuring photosynthetic activity of the photosynthetic tissue entrapped on the bio-trap 22. Applicants prefer a Walz XE-PAM pulse-amplitude-modulation fluorometer available from Heinz Walz GmbH•Eichenring 6•D−91090 Effeltrich•GERMANY Phone: +49-(0)9133/7765-0·Telefax: +49-(0)9133/5395•E-Mail: info @mail.wal. com. Other, less sensitive fluorometers should be sufficiently sensitive. The Walz XE-PAM fluorometer is described in detail at the following Internet web site:

http://www.walz.com/pamzta.htm

The fluorometer is electrically connected by a connector 32 to an electronics package 30, which includes a power supply, systems for operating the fluorometer 12 and pump 24, data processing electronics, and a transmitter that transmits a signal through an antenna 34. The electronics package 30 contains commonly used devices that are well known in the art. The particular components that are used therein, and the particular method of gathering, processing, and transmitting data are not critical to the operation of the present invention.

Operation of the biosensor 10 can be constant sampling or intermittent sampling. Intermittent operation can be random sampling or timed sampling. The pump 24 is operated to cause air to flow through the cell 14. The fluorometer 12 is activated to measure fluorescence in the cell 14. The electronics package 30 analyzes raw data from the fluorometer 12, and emits a signal through the antenna 34 indicating the presence and/or absence of chemical warfare agent(s) in the air. The signal is received by equipment that indicates and/or records the data. This type equipment and methods of use thereof are well known and can be easily applied to the present invention.

In one embodiment of the invention as shown schematically in FIG. 5, the biosensor is contained in an artillery shell 50. In step A, the artillery shell 50 has been fired and is approaching a preselected target zone. In step B, the artillery shell 50 has opened, and the biosensor 10 is released. A parachute 52 is preferable for allowing measurements to be taken as the biosensor 10 falls earthward. In step C, the biosensor 10 is testing the air and is transmitting data. The data is received by equipment located in a safe area that indicates and/or records the data.

While there has been shown and described what are at present considered the preferred embodiments of the invention, it will be obvious to those skilled in the art that various changes and modifications can be prepared therein without departing from the scope of the inventions defined by the appended claims.

What is claimed is:

1. A tissue-based, deployable, standoff air quality sensor for detecting the presence of at least one chemical or biological warfare agent comprising: a deployable cell containing entrapped photosynthetic tissue, said cell comprising a fluorometer for analyzing photosynthetic activity of said entrapped photosynthetic tissue; means for introducing an air sample into said cell and contacting said air sample with said entrapped photosynthetic tissue; and transmitting means for transmitting analytical data generated by said fluorometer relating to the presence of at least one chemical or biological warfare agent in said air sample, wherein said data is based upon changes in the photosynthetic activity of said entrapped tissue.

2. A sensor in accordance with claim 1 wherein said sensor is deployable by dropping from an aircraft.

3. A sensor in accordance with claim 1 wherein said sensor is deployable by a projectile.

4. A sensor in accordance with claim 3 wherein said projectile comprises an artillery projectile.

5. A method of testing air to detect the presence of at least one chemical or biological warfare agent comprising the steps of:
   a. deploying a tissue-based, deployable, standoff air quality sensor into an area of suspected presence of at least one chemical or biological warfare agent, so tat said sensor, upon deployment tests the air for the presence of at least one chemical or biological warfare agent by:
      (1) contacting an air sample with photosynthetic organisms entrapped in said sensor
      (2) analyzing photosynthetic activity of said entrapped photosynthetic organisms; and
      (3) transmitting analytical data relating to the of at least one chemical or biological warfare agent in said air sample, wherein said data is based upon changes in the photosynthetic activity of said entrapped organisms; and
   b. receiving said data.

6. A method in accordance with claim 5 wherein said sensor is deployed by dropping from an aircraft.

7. A method in accordance with claim 5 wherein said sensor is deployed by delivering a projectile.

8. A method in accordance with claim 7 wherein said projectile comprises an artillery projectile.

* * * * *